United States Patent
Riondel et al.

(10) Patent No.: US 9,018,410 B2
(45) Date of Patent: Apr. 28, 2015

(54) METHOD FOR THE PRODUCTION OF 2-OCTYL ACRYLATE BY MEANS OF TRANSESTERIFICATION

(71) Applicant: Arkema France, Colombes (FR)

(72) Inventors: Alain Riondel, Forbach (FR); Coralie Graire, Grezieu-la-Varenne (FR); Marc Esch, Freyming-Merlebach (FR); Reinhard Linemann, Saarbrucken (DE)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/370,223

(22) PCT Filed: Jan. 14, 2013

(86) PCT No.: PCT/FR2013/050078
§ 371 (c)(1),
(2) Date: Jul. 2, 2014

(87) PCT Pub. No.: WO2013/110876
PCT Pub. Date: Aug. 1, 2013

(65) Prior Publication Data
US 2014/0371482 A1 Dec. 18, 2014

(30) Foreign Application Priority Data

Jan. 23, 2012 (FR) ...................................... 12 50607
Jul. 5, 2012 (FR) ...................................... 12 56471

(51) Int. Cl.
C07C 67/02 (2006.01)
C07C 67/293 (2006.01)

(52) U.S. Cl.
CPC ..................................... C07C 67/293 (2013.01)

(58) Field of Classification Search
USPC ......................................................... 560/217
See application file for complete search history.

(56) References Cited

U.S. PATENT DOCUMENTS 6,977,310 B2 12/2005 Ackermann et al.
7,265,251 B2 9/2007 Geisendoerfer et al.

FOREIGN PATENT DOCUMENTS

EP 960877 12/1999

OTHER PUBLICATIONS

Danni Liu et al, Rational Design of Pseudozyma Antarctica Lipase B Yielding a General Esterfication Catalyst, CHEMBIOCHEM, vol. 11, No. 6, Apr. 12, 2010, pp. 789-795.

*Primary Examiner* — Jafar Parsa
(74) *Attorney, Agent, or Firm* — Lynn B. Morreale

(57) ABSTRACT

The invention relates to the production of 2-octylacrylate of high purity and in good yield using ethyl titanate in solution in 2-octanol or 2-octyl titanate as a transesterification catalyst.

9 Claims, 2 Drawing Sheets

METHOD FOR THE PRODUCTION OF 2-OCTYL ACRYLATE BY MEANS OF TRANSESTERIFICATION

CROSS-REFERENCE TO RELATED APPLICATIONS

This application is a national stage application under 35 U.S.C. §371 of PCT/FR2013/050078, filed Jan. 14, 2013, which claims benefit to French patent application FR 1250607, filed Jan. 23, 2012 and French patent application FR 1256471, filed Jul. 5, 2012.

FIELD OF THE INVENTION

The present invention relates to the production of 2-octyl acrylate according to a continuous process by transesterification.

TECHNICAL BACKGROUND

It is known to produce acrylic esters by carrying out a transesterification reaction between an acrylate of a light alcohol (known as light acrylate) and a heavy alcohol.

This reaction is an equilibrated catalyzed reaction with generation of light alcohol, according to the formula (I):

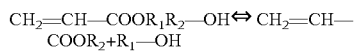

$$CH_2=CH-COOR_1 + R_2-OH \Leftrightarrow CH_2=CH-COOR_2 + R_1-OH$$

It is necessary to remove the light alcohol produced during the reaction in order to shift the equilibrium in the direction of the production of the acrylic ester.

This reaction is generally accompanied by side reactions which produce impurities which is necessary to remove for the purpose of obtaining the acrylic ester with a high purity satisfying the technical requirements related to its final use as monomer to manufacture polymers which can be used in numerous fields of application.

Furthermore, for obvious economic reasons, the economically upgradeable products present in the crude reaction mixture, in particular the unreacted reactants and the catalyst, are, as far as possible, recycled within the process.

For these purposes, a separation/purification process comprising a combination of distillations, extractions and/or separations by settling is generally performed, which process is simultaneously relatively complex to carry out, in particular as a result of the presence of azeotropic mixtures, and expensive energetically.

Various transesterification processes for producing acrylic esters have already been described in the prior art.

Mention may be made, for example, of the document U.S. Pat. No. 7,268,251, in which the reaction effluent from the transesterification is treated in the following way:

either most of the desired acrylic ester is first of all separated and is subsequently isolated from the catalyst used by distillation (separation of catalyst), or it is first of all isolated from the catalyst used by distillation (separation of catalyst) and subsequently most of the acrylic ester is separated, and, subsequently, the compounds having a lower boiling point than that of the desired acrylic ester are separated by distillation of the mixture obtained (separation of low-boiling-point substances) and subsequently the acrylic ester is distilled (distillation in the pure state).

This process requires the use of at least four distillation or rectification columns, including an evaporator in order to separate the catalyst, generally a titanium alkoxide.

Even if the process described in the document U.S. Pat. No. 7,268,251 relates to the manufacture of alkyl acrylates by transesterification starting from an alkyl acrylate and from an alcohol exhibiting a chain length greater by at least one carbon with respect to the alkyl chain of the starting acrylate, this process is illustrated only with the manufacture of dimethylaminoethyl acrylate from dimethylaminoethanol and methyl acrylate or ethyl acrylate in a cascade of two reactors.

It turns out that the process described in the document U.S. Pat. No. 7,268,251 is complicated to carry out on the industrial scale, as a result of the optimization of the operating conditions of the succession of the four distillation/rectification components, in order to obtain a product of high purity and a satisfactory productive output.

The document U.S. Pat. No. 6,977,310 describes a process for the continuous manufacture of (meth)acrylic acid alkyl esters from methyl(meth)acrylate and from a $C_2$-$C_{12}$ alcohol in the presence of a tetraalkyl titanate as transesterification catalyst. This process consists in subjecting the reaction mixture to a distillation under reduced pressure which separates the easily volatile compounds (unreacted reactants) and then the resulting fraction exiting at the column bottom, comprising the ester produced, the catalyst, the polymerization inhibitors and the high-boiling-point byproducts, is sent to a vacuum distillation stage which makes it possible to recover, at the top, the ester produced of high purity. According to this process, illustrated solely with the manufacture of butyl methacrylate or of isobutyl methacrylate, the desired methacrylate occurs in the bottom stream from the first distillation column under reduced pressure before being separated from the catalyst and purified.

The document EP 960 877, on behalf of the applicant company, illustrates another process for the manufacture of dimethylaminoethyl acrylate, more generally of dialkylaminoalkyl acrylate, by transesterification starting from dimethylaminoethanol and from methyl acrylate or ethyl acrylate.

This process consists of a removal of the catalyst and heavy products (tailing), followed by a removal of the light compounds (topping) and by a final rectification of a crude transesterification reaction mixture obtained using a catalyst chosen from tetrabutyl, tetraethyl and tetra(2-ethylhexyl) titanates. This process thus exhibits the advantage of comprising only three distillation columns in the purification train for the reaction mixture.

However, the process described in the document EP 960 877 is not applicable to the manufacture of a long-chain alkyl acrylate, for example 2-octyl acrylate, by transesterification reaction of a light acrylate with 2-octanol. This is because the transesterification of the titanates, either with a light alcohol released during the reaction or with the starting 2-octanol, brings about the appearance of impurities, such as butyl acrylate or 2-ethylhexyl acrylate, in the reaction mixture or in the light ester/light alcohol azeotropic mixture and complicates the purification of the 2-octyl acrylate.

A need thus still remains to have available a process for the manufacture of 2-octyl acrylate which exhibits a productive output compatible with manufacture on the industrial scale and which results in a 2-octyl acrylate meeting the purity requirements related to its final use, in particular with regard to the possibility of using this monomer in the manufacture of latexes having a low content of volatile organic compounds.

The applicant company has sought to solve the various problems of the abovementioned processes, in particular those related to the use of 2-octanol in the transesterification reaction, in order to produce 2-octyl acrylate of very high purity with a high yield, while including the recycling of the economically upgradeable products, such as the unreacted reactants and the catalyst.

The solution provided consists in using ethyl titanate in solution in 2-octanol or 2-octyl titanate as transesterification catalyst and in employing a purification train comprising a preliminary separation of the catalyst by distillation, followed by purification using at least one distillation column.

The present invention makes it possible in addition to produce an acrylic ester comprising carbon of renewable origin related to the use of the 2-octanol, which is an alcohol derived from plant matter.

SUMMARY OF THE INVENTION

A subject matter of the present invention is a process for the continuous production of 2-octyl acrylate by a transesterification reaction between a light alcohol acrylate and 2-octanol in the presence of an alkyl titanate as transesterification catalyst and at least one polymerization inhibitor, the azeotropic mixture composed of light alcohol acrylate and of light alcohol generated by the transesterification reaction being withdrawn continuously during the reaction, the reaction mixture being subjected to a purification treatment comprising at least two distillation columns, in order to obtain, on the one hand, the pure 2-octyl acrylate and, on the other hand, the unreacted 2-octanol and light alcohol acrylate compounds intended to be recycled, and also the catalyst intended to be recycled, which process is characterized in that:
  (i) the catalyst is chosen from ethyl titanate in solution in 2-octanol and 2-octyl titanate;
  (ii) a preliminary separation of the catalyst is carried out by sending, to a first distillation column (C1) under reduced pressure, the crude reaction mixture comprising the desired 2-octyl acrylate with, as light products, the unreacted 2-octanol and light alcohol acrylate and, as heavy products, the catalyst, the polymerization inhibitor or inhibitors and also heavy reaction products, and a distillation is carried out, in said first column (C1), which makes it possible to obtain:
    at the top, a stream composed essentially of 2-octyl acrylate and light products, comprising a minor fraction of polymerization inhibitors but devoid or substantially devoid of catalyst, and
    at the bottom, a stream of heavy reaction products with the catalyst, the polymerization inhibitor(s) and a minor fraction of 2-octyl acrylate, said stream being recycled to the reaction stage; then
  (iii) by distillation of the top stream from the first distillation column (C1), the unreacted 2-octanol and light alcohol acrylate compounds, a fraction comprising polymerization inhibitors and the pure 2-octyl acrylate are separated;
  (iv) the desired pure 2-octyl acrylate is recovered;
  (v) the unreacted 2-octanol and light alcohol acrylate compounds are recycled to the reaction stage;
  (vi) a fraction comprising polymerization inhibitors is sent to the column (C1) for separation of the catalyst.

According to a first embodiment of the invention, stage (iii) of the process is carried out from the following two substages (iii1) and (iii2):
  (iii1) the top stream from the first distillation column (C1) is sent to a second distillation column (C2) under reduced pressure, in which a distillation is carried out which makes is possible to obtain:
    at the top, a stream composed essentially of unreacted 2-octanol and light alcohol acrylate, with a minor fraction of 2-octyl acrylate; and
    at the bottom, 2-octyl acrylate comprising traces of unreacted products and of polymerization inhibitors; then
  (iii2) the bottom stream from the second distillation column (C2) is sent to a third distillation column (C3) under reduced pressure, in which a rectification is carried out which makes it possible to separate:
    at the top, the desired pure 2-octyl acrylate; and
    at the bottom, the polymerization inhibitors in solution in 2-octyl acrylate.

According to a second embodiment of the invention, stages (iii) and (iv) of the process are carried out simultaneously by sending the top stream from the first column (C1) to a second column (C2') under reduced pressure, in which a distillation is carried out which makes it possible to obtain:
    at the top, a stream composed essentially of unreacted 2-octanol and light alcohol acrylate, with a minor fraction of 2-octyl acrylate;
    at the bottom, a stream comprising the polymerization inhibitors with a fraction of 2-octyl acrylate:
and to recover the desired pure 2-octyl acrylate via a side stream.

The invention is now described in more detail and without implied limitation in the description which follows, with reference to the appended FIGS. 1 and 2, which diagrammatically represent a plant which makes it possible to implement the process according to the invention respectively according to the first embodiment described above and according to the second embodiment described above.

DETAILED DESCRIPTION

Figure 1:
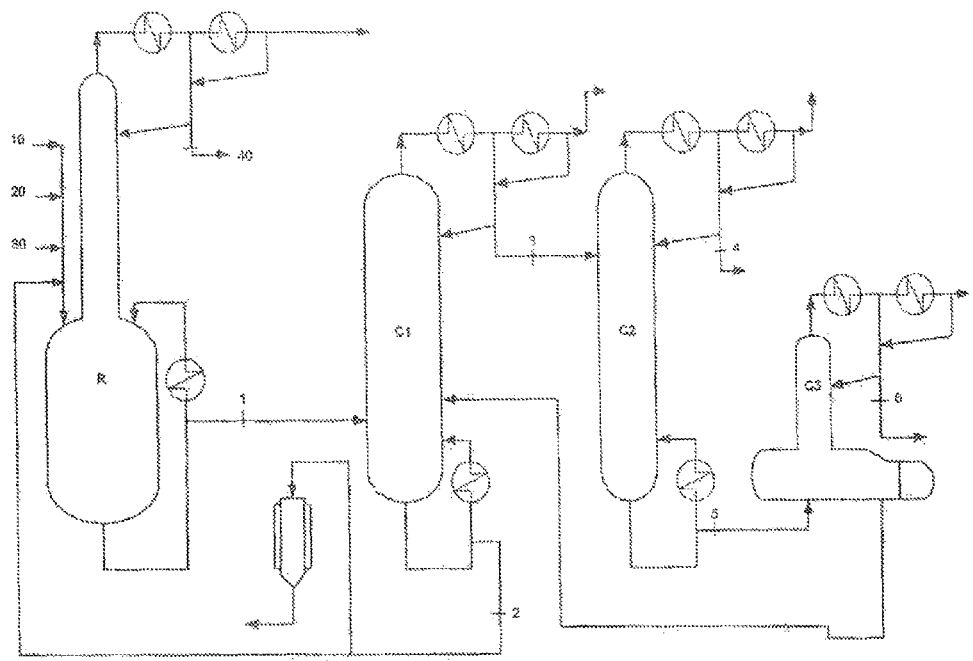
FIG. 1 is a schematic representation of a plant suitable to implement a first embodiment of the inventive process.

One of the objectives of the invention is to use starting materials of natural and renewable origin, that is to say biosourced.

The 2-octanol used in the process according to the invention is an alcohol of renewable origin; in particular, it can be obtained by alkaline treatment of ricinoleic acid derived from castor oil.

The light alcohol acrylate employed as starting material in the process according to the invention is obtained by direct esterification of acrylic acid, essentially produced industrially from propylene, with a light alcohol, generally methanol or ethanol.

Independently of the use of 2-octanol of renewable origin, the invention extends to the use of a light alcohol acrylate derived from acrylic acid of renewable origin, which can in particular be obtained from glycerol, according to a process comprising a first stage of dehydration of the glycerol to give acrolein, followed by a stage of gas-phase oxidation of the acrolein thus obtained, or obtained by dehydration of 2-hydroxypropionic acid (lactic acid) or 3-hydroxypropionic acid and their esters.

The invention also extends to the use of a light alcohol acrylate derived from a biosourced alcohol, such as bioethanol.

Generally, the transesterification reaction is carried out in a stirred reactor (R) with a light alcohol acrylate/2-octanol molar ratio which can range from 1 to 3, preferably between 1.3 and 1.8.

Use is made, as light alcohol acrylate, of methyl acrylate, ethyl acrylate or butyl acrylate, preferably ethyl acrylate.

The transesterification catalyst is ethyl titanate in solution in 2-octanol, for example a 90% solution of ethyl titanate in 2-octanol, or 2-octyl titanate, obtained beforehand by reaction of ethyl titanate with 2-octanol at 100° C., preferably 2-octyl titanate.

The catalyst is used in a proportion of $5 \times 10^{-4}$ to $5 \times 10^{-2}$ mol per mole of 2-octanol, preferably in a proportion of $10^{-3}$ to $10^{-2}$ mol per mole of 2-octanol.

The transesterification reaction is generally carried out in the reactor (R) at a pressure of between 500 mmHg and atmospheric pressure and at a temperature ranging from 90° C. to 130° C., preferably from 100° C. to 120° C.

The reaction is carried out in the presence of one or more polymerization inhibitors which are introduced into the reactor, in a proportion of 1000 to 5000 ppm with respect to the crude reaction mixture. Mention may be made, as polymerization inhibitors which can be used, for example, of phenothiazine, hydroquinone, hydroquinone monomethyl ether, di(tert-butyl)-para-cresol (BHT). TEMPO (2,2,6,6-tetramethyl-1-piperidinyloxy), di(tert-butyl)catechol or TEMPO derivatives, such as 4-hydroxy(OH)-TEMPO, alone or their mixtures in all proportions. A further addition of polymerization inhibitor is generally carried out in the subsequent purification treatment, in particular in each of the distillation columns.

The light alcohol formed by the transesterification reaction is continuously entrained by distillation into a column surmounting the reactor in the form of an azeotropic mixture with the light alcohol acrylate.

After reaction with a residence time in the reactor generally of between 3 and 6 hours, the crude reaction mixture (1) comprises the desired 2-octyl acrylate with, as light products, the unreacted 2-octanol and light alcohol acrylate and, as heavy products, the catalyst, the polymerization inhibitor or inhibitors and also heavy reaction byproducts.

With reference to FIG. 1, the reaction mixture is subjected to a purification treatment which can comprise three distillation columns (C1), (C2) and (C3), in order to obtain, on the one hand, the pure 2-octyl acrylate (column C3) and, on the other hand, the unreacted 2-octanol and light alcohol acrylate compounds intended to be recycled (column C2), and also the catalyst intended to be recycled (column C1).

Figure 2:
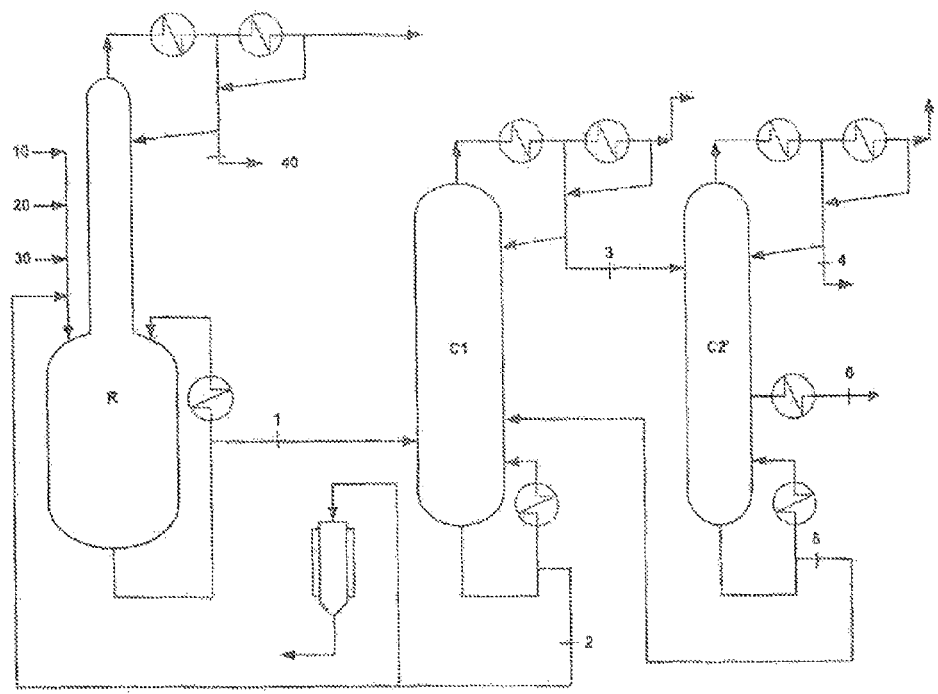
FIG. 2 is a schematic representation of a plant suitable to implement a second embodiment of the inventive process.

In an alternative form and as illustrated by FIG. 2, the purification treatment comprises only two distillation columns (C1) and (C2') which separate the catalyst intended to be recycled (column C1), the desired pure 2-octyl acrylate and the unreacted 2-octanol and light alcohol acrylate compounds intended to be recycled (column C2').

The first distillation column (C1) generally operates under a pressure ranging from 20 to 50 mmHg ($0.027 \times 10^5$ Pa to $0.067 \times 10^5$ Pa) at a bottom temperature ranging from 120° C. to 150° C.

The column (C1) bottom stream (2) is composed of the catalyst, heavy byproducts, 2-octyl acrylate and polymerization inhibitors. This stream is advantageously recycled in part to the reaction, the other part being removed via a film evaporator in order to prevent an accumulation of heavy fraction in the plant.

The column (C1) top stream (3) is thus devoid or substantially devoid of catalyst and heavy products and it is composed essentially of the desired 2-octyl acrylate and unreacted light products (light alcohol acrylate and 2-octanol).

According to the first embodiment of the invention illustrated in FIG. 1, this stream (3) is subjected to a distillation in a second distillation column (C2) which generally operates under a pressure of 20 to 50 mmHg ($0.027 \times 10^5$ Pa to $0.067 \times 10^5$ Pa) and a bottom temperature ranging from 120° C. to 150° C.

The top stream (4) from the column (C2) is essentially composed of unreacted 2-octanol and light alcohol acrylate, with a minor fraction of 2-octyl acrylate; it is advantageously recycled to the reaction.

At the bottom of the column (C2), 2-octyl acrylate comprising traces of unreacted products and heavy byproducts, and the polymerization inhibitor or inhibitors, is obtained in a stream (5).

The stream (5) is purified on a third distillation column (C3) which generally operates under a pressure ranging from 20 to 50 mmHg ($0.027 \times 10^5$ Pa to $0.067 \times 10^5$ Pa) at a temperature ranging from 120 to 150° C.

The polymerization inhibitors separated in the bottom stream of the column (C3) are advantageously recycled, in particular in the column (C1).

The pure 2-octyl acrylate (6) is recovered at the top of the column (C3). The purity is greater than 99.5%, indeed even greater than 99.8%.

According to the second embodiment of the invention illustrated in FIG. 2, the stream (3) is subjected to a distillation in a second distillation column (C2') which generally operates under a pressure to 20 to 50 mmHg ($0.027 \times 10^5$ Pa to $0.067 \times 10^5$ Pa) and a bottom temperature ranging from 120° C. to 150° C. The column (C2') is generally a distillation column comprising from 15 to 25 theoretical plates.

The operation of the column ((l2') is modified with respect to the operation of the column (C2): said column (C2') is provided with a side stream which makes it possible to extract, via the line 6 located at an intermediate level, the desired pure 2-octyl acrylate stream and, at the top, the stream (4) essentially composed of unreacted 2-octanol and light alcohol acrylate, this stream (4) advantageously being recycled to the reaction.

The stream (5), separated at the bottom of the column (C2'), essentially comprises 2-octyl acrylate with the polymerization inhibitors; this stream is advantageously recycled at the bottom of the column (C1).

The side stream of the desired pure product is generally taken in the liquid phase or in the gas phase, preferably in the gas phase, at an intermediate level located in the lower part of the column, in particular between the theoretical plates 14 and 24 for a number of theoretical plates of 15 to 25 of the column.

This embodiment is particularly advantageous since it employs only a single distillation column after the separation of the catalyst and since it results in a 2-octyl acrylate with a purity of greater than 99.8% being obtained.

The recycling of the catalyst, of the unreacted reactant products and of the polymerization inhibitors renders the process of the invention particularly efficient in terms of productive output.

The following examples illustrate the present invention without, however, limiting the scope thereof.

EXPERIMENTAL PART

In the examples, the percentages are shown by weight, unless otherwise indicated, and the following abbreviations have been used:
EA: ethyl acrylate
2OCTA: 2-octyl acrylate
PTZ: phenothiazine
HQME: hydroquinone methyl ester

Example 1

According to the Invention

Ethyl acrylate, 2-octanol and a mixture of ethyl titanate in solution in 2-octanol (90% mixture of ethyl titanate in 2-octanol) with phenothiazine inhibitor, in the proportions by weight 53.8/45.6/0.6, are charged to a perfectly stirred reactor R heated by an external exchanger and surmounted by a distillation column having 12 theoretical plates.

The reactor is heated, while bubbling with air, and, as soon as the temperature reaches 115° C. under 500 mmHg ($0.67 \times 10^5$ Pa), EA stabilized with 2000 ppm of PTZ (10), 2-octanol (20) and ethyl titanate in solution in 2-octanol (30), in proportions by weight 53.8/45.6/0.6, are continuously introduced.

At the column top, the EA/ethanol azeotrope (40), with a composition by weight of 35/65, is continuously withdrawn.

The crude reaction product (1), obtained by continuous reaction, comprises 2OCTA, unreacted EA, unreacted 2-octanol and a mixture comprising the catalyst with the polymerization inhibitors and heavy derivatives, in proportions by weight 73/20.1/6.3/0.6.

The stream (1) is sent continuously to a first distillation column C1 having 12 theoretical plates operating under reduced pressure and heated by an external exchanger at a temperature of 140° C.

At the column C1 top, a mixture comprising 2500 ppm of PTZ in EA is introduced.

The column C1 separates, at the top, an EA/2-octanol/2OCTA mixture (3) having the composition by weight 21/9/70 and, at the bottom, a mixture (2) comprising the heavy products, the polymerization inhibitors and the catalyst and a 2OCTA fraction.

The mixture (2) is returned in part to the reaction.

The mixture (3) is sent to a second distillation column C2.

The column C2, with 12 theoretical plates, is heated by an external exchanger and operates under a vacuum of 20 mmHg ($0.027 \times 10^5$ Pa) at the column top.

At the column C2 top, a mixture comprising 2500 ppm of PTZ in EA is introduced.

The column C2 separates, at the top, an EA/2-octanol/2OCTA mixture (4) having the composition by weight 60/25/15 and, at the bottom, a mixture (5) enriched in 2OCTA. The mixture (5) has the following composition:

| | |
|---|---|
| 2OCTA | 99.7% |
| EA | traces |
| 2-Octanol | 200 ppm |
| PTZ | 0.25% |
| Others | 300 ppm |

The mixture (4) is recycled to the reaction in the reactor R.

The mixture (5) is sent to a third distillation column C3. The column C3, having 12 theoretical plates, is heated by an exchanger and operates under a vacuum of 50 mmHg ($0.067 \times 10^5$ Pa) at the column top.

At the column C3 top, a mixture comprising 2500 ppm of HQME in 2OCTA is introduced.

The column C3 separates, at the top, 2OCTA (6) with a purity of 99.85%, the remaining reactants being present in the form of traces (2-octanol: 300 ppm).

The polymerization inhibitors separated at the bottom of the column C3 are advantageously recycled to the column C1

The low content of 2-octanol present in the pure 2-octyl acrylate is compatible with the manufacture of latexes having a low content of volatile organic compounds.

Example 2

Comparative

The same synthesis as in example 1 was carried out but using, as catalyst, butyl titanate as replacement for ethyl titanate.

In this case, the stream (4) distilled at the top of the column C2 comprises, in addition to the unreacted reactants with a minor fraction of 2OCTA, 15% of butyl acrylate originating from the reaction of the catalyst with the EA.

This stream (4), intended to be recycled to the reaction stage, required a preliminary purification by distillation on an additional column to remove the butyl acrylate, in order to limit the accumulation over time of butyl acrylate in the plant and the risk of contamination of the purified 2OCTA.

Example 3

Comparative

The same synthesis as in example 1 was carried out but using, as catalyst, 2-ethylhexyl titanate as replacement for ethyl titanate.

In this case, 2OCTA with a purity of 97.5% was obtained at the top of the column C3 due to the presence of 2% of 2-ethylhexyl acrylate originating from the catalyst in the purified product.

The 2-octyl acrylate thus obtained does not offer the same performance in pressure-sensitive adhesives as a 2OCTA having a purity of 99.8%.

Example 4

Comparative

Example 1 was repeated but while sending the crude reaction product (1) directly to the distillation column C2 and than sending the bottom fraction from the column C2 comprising the catalyst to the column C3.

In this case, 2OCTA comprising 500 ppm of EA and 1500 ppm of 2-octanol was obtained, the catalyst being removed at the bottom of the column C3.

Such a quality of 2OCTA is not suitable for coating applications having a very low content of volatile organic compounds.

Example 5

According to the Invention

The same synthesis as in example 1 was carried out but the stream 3 was sent to a column C2' comprising 15 theoretical plates provided with a side stream at plate 14. A pure 2OCTA with a purity of 99.85% was obtained, the remaining reactants being present in the form of traces (2-octanol: 300 ppm).

The invention claimed is:

1. A process for the continuous production of 2-octyl acrylate by a transesterification reaction between a light alcohol acrylate and 2-octanol using an alkyl titanate as transesterification catalyst and at least one polymerization inhibitor, an azeotropic mixture comprising light alcohol acrylate and light alcohol generated by the transesterification reaction being withdrawn continuously during the reaction, a crude reaction mixture being subjected to a purification treatment comprising at least two distillation columns, in order to obtain, on the one hand, substantially pure 2-octyl acrylate, and, on the other hand, unreacted 2-octanol and light alcohol acrylate compounds and also the catalyst all for recycle, wherein the process further comprises the steps of:

(i) choosing the catalyst is chosen from the group consisting of ethyl titanate in solution in 2-octanol and 2-octyl titanate;

(ii) sending to a first distillation column (C1) having a top and a bottom and under reduced pressure, the crude reaction mixture comprising 2-octyl acrylate with, as light products, the unreacted 2-octanol and light alcohol acrylate and, as heavy products, the catalyst, the polymerization inhibitor and heavy reaction products, for distillation in said first column (C1), to obtain:

at the top, a top stream consisting essentially of 2-octyl acrylate and light products, including a minor fraction of polymerization inhibitors but substantially devoid of catalyst, and at the bottom, a stream of heavy reaction products with the catalyst, the polymerization inhibitor and a minor fraction of 2-octyl acrylate, said stream being recycled to the reaction stage; then (iii) separating by distillation of the top stream from the first distillation column (C1), the unreacted 2-octanol and light alcohol acrylate compounds, a fraction comprising polymerization inhibitors and substantially pure 2-octyl acrylate;

(iv) recovering substantially pure 2-octyl acrylate;

(v) recycling unreacted 2-octanol and light alcohol acrylate compounds to the reaction;

(vi) sending a fraction comprising polymerization inhibitors to the column (C1) for separation of the catalyst.

2. The process as claimed in claim 1, wherein stage (iii) of the process is carried out from the following two substages (iii1) and (iii2):

(iii1) sending the top stream from the first distillation column (C1) to a second distillation column (C2) having a top and bottom and under reduced pressure for distillation to obtain:

at the top of C2, a stream consisting essentially of unreacted 2-octanol and light alcohol acrylate, with a minor fraction of 2-octyl acrylate; and at the bottom of C2, a bottoms stream of 2-octyl acrylate further comprising traces of unreacted products and polymerization inhibitors; then (iii2) sending the bottom stream from the second distillation column (C2) to a third distillation column (C3) having a top and a bottom and under reduced pressure, for rectification to separate:

at the top, substantially pure 2-octyl acrylate; and at the bottom, the polymerization inhibitors in solution in 2-octyl acrylate.

3. The process as claimed in claim 1, wherein stages (iii) and (iv) of the process are carried out simultaneously by sending the top stream from the first column (C1) to a second column (C2') under reduced pressure, in which a distillation is carried out to obtain:

at the top, a stream consisting essentially of unreacted 2-octanol and light alcohol acrylate, with a minor fraction of 2-octyl acrylate;

at the bottom, a stream comprising the polymerization inhibitors with a fraction of 2-octyl acrylate and of unreacted products;

and to recover substantially pure 2-octyl acrylate via a side stream.

4. The process as claimed in claim 1 wherein the catalyst is 2-octyl titanate.

5. The process of claim 1 wherein the catalyst is used in a proportion of $5\times10^{-4}$ to $5\times10^{-2}$ mol per mole of 2-octanol.

6. The process of claim 1 wherein the reaction is carried out starting from ethyl acrylate.

7. The process of claim 1 wherein the light alcohol acrylate/2-octanol molar ratio ranges from 1 to 3.

8. The process of claim 1 wherein the transesterification reaction is carried out at a pressure of between 500 mmHg ($0.67\times10^5$ Pa) and atmospheric pressure ($10^5$ Pa) and at a temperature ranging from 90° C. to 130° C.

9. The process of claim 1 wherein the light alcohol acrylate is ethyl acrylate of renewable origin.

* * * * *